US00PP27429P2

(12) United States Plant Patent
Danziger

(10) Patent No.: US PP27,429 P2
(45) Date of Patent: Nov. 29, 2016

(54) ***VERBENA* PLANT NAMED 'DVERTOPRED'**

(50) Latin Name: *Verbena hybrida*
Varietal Denomination: DVERTOPRED

(71) Applicant: Gavriel Danziger, Moshav Mishmar Hshiva (IL)

(72) Inventor: Gavriel Danziger, Moshav Mishmar Hshiva (IL)

(73) Assignee: Danziger 'DANZIGER Flower Farm (IL)

( * ) Notice: Subject to any disclaimer, the term of this patent is extended or adjusted under 35 U.S.C. 154(b) by 6 days.

(21) Appl. No.: 14/545,410

(22) Filed: Apr. 30, 2015

(51) Int. Cl.
*A01H 5/02* (2006.01)

(52) U.S. Cl.
USPC ..... Plt./308

(58) Field of Classification Search
USPC ..... Plt./308
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Verbena* cultivar named 'DVERTOPRED' is disclosed, characterized by a compact, semi-upright growth habit, moderate fragrance, tolerance to powdery mildew and an abundance of red flowers. Additionally the new variety is tolerant to high temperatures. The new variety is a *Verbena*, normally produced as an outdoor garden or container plant.

2 Drawing Sheets

Figure 1:
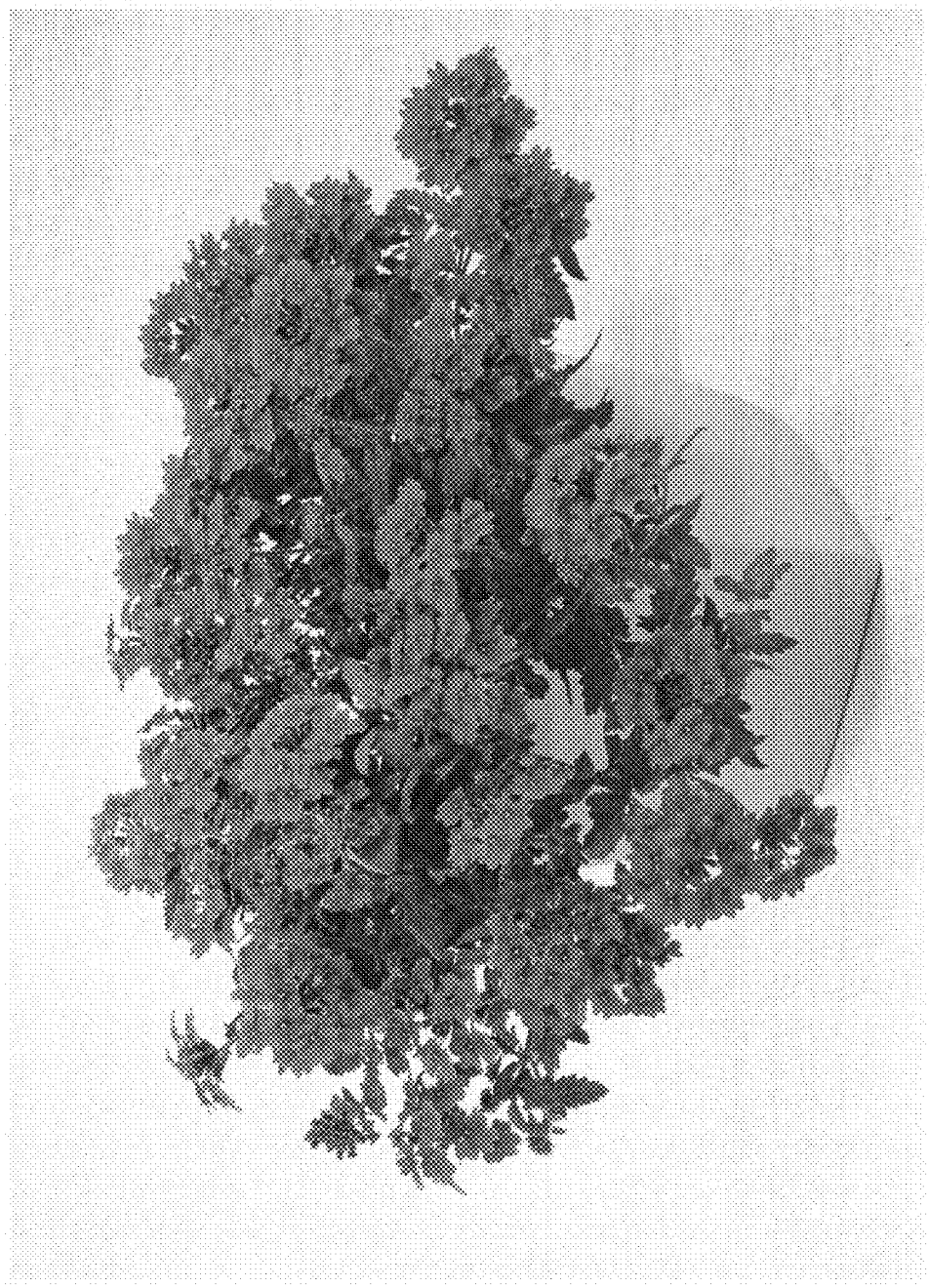

Latin name of the genus and species: *Verbena hybrida.*
Variety denomination: 'DVERTOPRED'.

BACKGROUND OF THE INVENTION

The new *Verbena* cultivar is a product of a planned breeding program conducted by the inventor, Gavriel Danziger, in Moshav Mishmar Hashiva, Israel. The objective of the breeding program was to produce new *Verbena* varieties for ornamental commercial applications. The cross resulting in this new variety was made during October of 2011.

The seed parent is the, unpatented, proprietary variety referred to as *Verbena* 'VE-Z-279'. The pollen parent is the unpatented, propriety variety referred to as *Verbena* 'VE-11-6071'. The new variety was discovered in July of 2012 by the inventor in a group of seedlings resulting from the 2011 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in July of 2012 and has shown that the unique features of this cultivar are stable and reproduced true to type in more than 10 successive generations.

SUMMARY OF THE INVENTION

The cultivar 'DVERTOPRED' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVERTOPRED' These characteristics in combination distinguish 'DVERTOPRED' as a new and distinct *Verbena* cultivar:

1. Moderately fragrant flowers.
2. Semi-upright, compact plant habit.

3. Moderate tolerance for powdery mildew.
4. Highly floriferous plants producing an abundance of red flowers.

Plants of the new cultivar 'DVERTOPRED' are similar to plants of the seed parent, *Verbena* 'VE-Z-279' in most horticultural characteristics, however, plants of the new cultivar 'DVERTOPRED' differ in the following;

1. Compact, semi-upright growth habit, whereas the seed parent has a mounded growth habit.
2. Tolerates powdery mildew, whereas the seed parent is sensitive to powdery mildew.
3. Flowers have a delicate fragrance whereas the seed parent has no fragrance.
4. The new variety produces more flowers per plant.
5. Clear red flowers, whereas the seed parent flowers are dark red.

Plants of the new cultivar 'DVERTOPRED' are similar to plants of the pollen parent, *Verbena* 'VE-11-6071' in most horticultural characteristics, however, plants of the new cultivar 'DVERTOPRED' differ in the following;

1. Clear red flowers, whereas the pollen parent flowers are dark red
2. Earlier flowering than the pollen parent.
3. Less branches per plant than the highly branched pollen parent.
4. Less vigorous than the pollen parent.

COMMERCIAL COMPARISON

Plants of the new cultivar 'DVERTOPRED' are comparable to the unpatented commercial variety *Verbena* 'Vepita Fire Red'. The two *Verbena* varieties are similar in most horticultural characteristics; however, the new variety 'DVERTOPRED' differs in the following:

1. Larger flowers than the comparator.
2. Trailing growth habit. The comparator growth habit is mounded.

3. Clear red flowers. The comparator flowers are dark red.
4. Tolerant of powdery mildew. The comparator is sensitive to powdery mildew.

BRIEF DESCRIPTION OF THE PHOTOGRAPHS

The accompanying photograph in FIG. 1 illustrates in full color a typical plant of 'DVERTOPRED' grown in a nursery, in a 13 cm pot. Age of the plant photographed is approximately 9 weeks from a rooted cutting.

Figure 2:
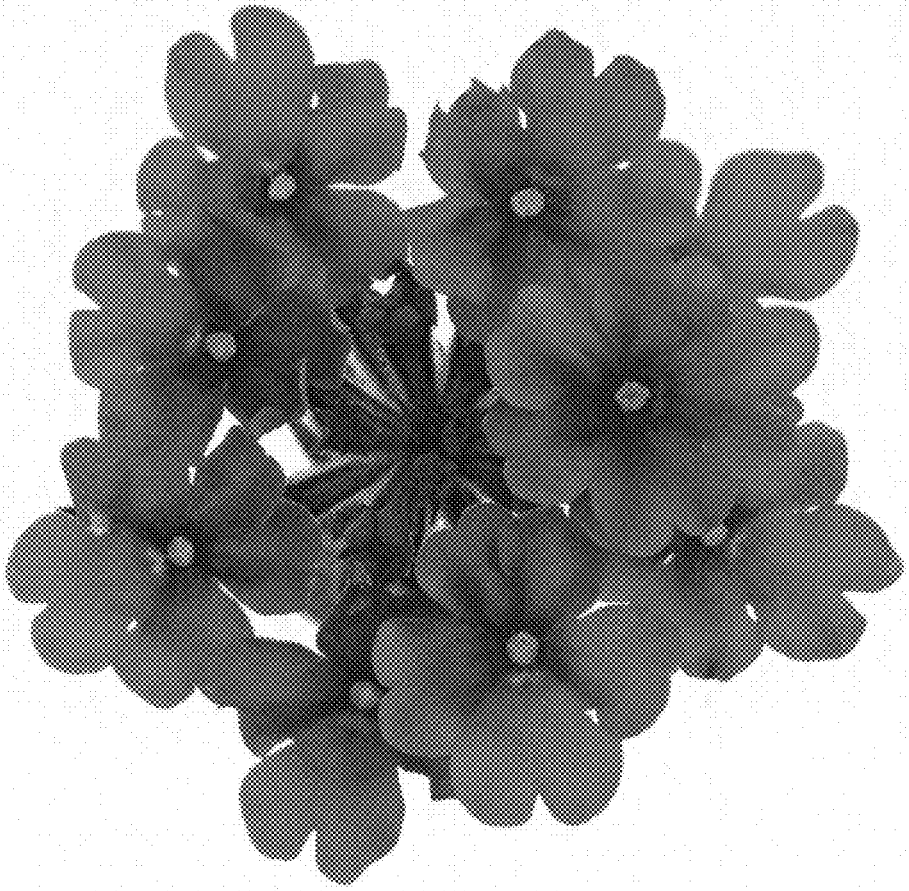

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DVERTOPRED' plants grown outdoors during the Spring, in Moshav Mishmar Hashiva, Israel. The growing temperature ranged from 18° C. to 27° C. during the day and from 10° C. to 15° C. during the night. General light conditions are bright, normal sunlight. Measurements and numerical values represent averages of typical plant types.

Botanical classification: *Verbena* 'DVERTOPRED'.

PROPAGATION

Type of propagation typically used: Cutting.
Time to initiate roots: 4-5 days.
Root description: Fibrous.

PLANT

Age of plant described: Approximately 60 days from a rooted cutting.
Pot size of plant described: 12 cm.
Growth habit: Semi-upright, compact.
Height: Approximately 15 cm.
Plant spread: 30 cm.
Growth rate: Fast.
Branching characteristics: Freely branching.
Characteristics of primary lateral branches:
- *Quantity of primary lateral branches.*—10.
- *Length of primary lateral branches.*—22 cm.
- *Form.*—Cylindrical.
- *Diameter.*—0.3 cm.
- *Color.*—RHS Yellow-green 144 A.
- *Texture.*—Pubescent.
- *Strength.*—Flexible.

Internode length: 2.5-3.0 cm.

FOLIAGE

Leaf:
- *Arrangement.*—Opposite.
- *Quantity.*—Approximately 20 per branch.
- *Average length.*—5.0 cm.
- *Average width.*—2.5 cm.
- *Shape of blade.*—Deltate.
- *Apex.*—Cuspidate.
- *Base.*—Cordate.
- *Margin.*—Crenate, irregular.
- *Texture of top surface.*—Pubescent.
- *Pubescence.*—Strigose.
- *Aspect.*—45 degrees.
- *Color.*—Young foliage upper side: RHS Green 137 D. Young foliage under side: RHS Yellow-green 147 B. Mature foliage upper side: RHS Green N 137 B. Mature foliage under side: RHS Yellow-green 147 B.
- *Venation.*—Type: Arcute. Venation color upper side: RHS Yellow-green 147 B. Venation color under side: RHS Yellow-green 147 D.
- *Petiole.*—Length: 1.2 cm. Diameter: 0.2 cm. Color: RHS Yellow-green 144 B. Texture: Pubescent.

FLOWER

Natural flowering season: Spring-Summer.
Days to flowering from rooted cutting: 16 days.
Inflorescence and flower type and habit: Terminal Cluster.
Rate of flower opening: 4 to 6 days from bud to fully opened flower.
Flower longevity on plant: 5 days.
Persistent or self-cleaning: Self-cleaning.

Bud:
- *Shape.*—Quinquangular.
- *Length.*—1 cm.
- *Diameter.*—0.2 cm.
- *Color.*—RHS Green 137 B.

Corolla:
- *Flower.*—Depth: 1.6-1.8 cm. Diameter: 0.1 cm.
- *Petals/lobes.*—Number: 5. Length: 1 cm. Width: 0.8 cm. Shape: Obcordate. Aspect: Upright. Margin: Entire. Texture: Smooth. Color: When opening: Upper surface: RHS Red 46 A. Lower surface: RHS Red 53 B. Fully opened: Upper surface: RHS Red 45 A. Lower surface: RHS Red 45 C. Throat: Color: RHS Yellow 8 D. Texture: Smooth. Tube color: RHS Yellow 8 C.

Calyx:
- *Diameter.*—0.1 cm.
- *Sepal shape.*—Five sepals whose margins are fused-quinquangular.
- *Sepal margin.*—Entire.
- *Sepal texture.*—Pubescent.
- *Sepal color.*—Upper surface: RHS Yellow-green 146 A. Lower surface: RHS Yellow-green 146 C.

Fragrance: Moderate floral fragrance.

Pedicels:
- *Length.*—2.5 cm.
- *Diameter.*—0.2 cm.
- *Color.*—RHS Yellow-green 147 B.
- *Texture.*—Pubescent.

REPRODUCTIVE ORGANS

Stamens:
- *Number (per flower).*—4.
- *Filament length.*—0.15 cm.
- *Anthers.*—Shape: Conical. Length: 0.5 cm. Color: RHS Yellow 2 B.

Pollen:
- *Color.*—RHS Yellow 2 A.
- *Amount.*—Abundant.

Pistils:

*Quantity per flower.*—1.

*Length.*—0.75 cm.

*Styles.*—Length: 0.05 cm. Color: RHS Yellow 2 D. Stigma: Shape: Ovoid. Color: RHS Yellow-green 151 B.

OTHER CHARACTERISTICS

Seeds and fruits: Low number of seeds produced. Minute, elliptic shaped, dry to nearly papery. Brown, not accurately measured by RHS chart, due to size.

Disease/pest resistance: Tolerates to powdery mildew. Neither resistance nor susceptibility to other diseases and pests have been observed.

Temperature tolerance: Tolerates temperatures from approximately −1° C. to 32° C.

What is claimed is:

1. A new and distinct cultivar of *Verbena* plant named 'DVERTOPRED' as herein illustrated and described.

* * * * *